United States Patent [19]

Kisumi et al.

[11] Patent Number: 4,692,409
[45] Date of Patent: Sep. 8, 1987

[54] METHOD FOR PRODUCING L-ASPARTIC ACID

[75] Inventors: Masahiko Kisumi, Kobe; Saburo Komatsubara, Kusatsu; Tomoyasu Taniguchi, Izumiohtsu, all of Japan

[73] Assignee: Tanabe Seiyaku Co., Ltd., Osaka, Japan

[21] Appl. No.: 615,290

[22] Filed: May 30, 1984

[30] Foreign Application Priority Data

Jun. 15, 1983 [JP] Japan .................................. 58-107573

[51] Int. Cl.$^4$ ...................... C12P 13/20; C12N 15/00; C12N 1/20; C12N 1/00
[52] U.S. Cl. .................................. 435/109; 435/172.3; 435/253; 435/317; 935/60; 935/73
[58] Field of Search ..................... 435/109, 172.3, 253, 435/317; 935/29, 60, 73

[56] References Cited

U.S. PATENT DOCUMENTS 4,326,029 4/1982 Yukawa et al. .................... 935/38 X
4,430,430 2/1984 Momose et al. .................... 435/114

FOREIGN PATENT DOCUMENTS 0129119 12/1984 European Pat. Off. ............ 435/109

OTHER PUBLICATIONS

Komatsubara, S. et al., *J. Biotechnology*, vol. 3, pp. 281–291, 1986.
Guest, J. et al., *J. of Gen. Microbiol.*, vol. 130, pp. 1271–1278, May, 1984.
Spencer, M. et al., *J. of Gen. Microbiol.*, vol. 97, pp. 73–82, 1976.
Takagi, J. et al., *Nuc. Acids Res.*, vol. 13, No. 6, pp. 2063–2074, 1985.

*Primary Examiner*—Thomas G. Wiseman
*Assistant Examiner*—Jayme A. Huleatt
*Attorney, Agent, or Firm*—Scully, Scott, Murphy & Presser

[57] ABSTRACT

A novel microorganism of the genus Escherichia containing a hybrid plasmid prepared by integrating a plasmid with a deoxyribonucleic acid carrying the gene for aspartase which is obtained from a microorganism of the genus Escherichia. An industrially advantageous method for producing L-aspartic acid comprising contacting a culture of the novel microorganism, microbial cells collected from the culture or a processed material of the microbial cells with fumaric acid and ammonia to produce L-aspartic acid and then collecting L-aspartic acid thus produced is also disclosed.

3 Claims, No Drawings

METHOD FOR PRODUCING L-ASPARTIC ACID

FIELD OF THE INVENTION

The present invention relates to a novel microorganism of the genus Escherichia having high aspartase activity and a method for producing L-aspartic acid using the microorganism.

BACKGROUND OF THE INVENTION

It has hitherto been known that *Escherichia coli* has aspartase activity, and a method of enzymatic production of L-aspartic acid from ammonium fumarate (or fumaric acid and an ammonium salt) by using such a microorganism has been also known in the prior art [Bull. Agr. Chem. Soc. Japan, 24, 296 (1960); Appl. Microbiol., 27, 886 (1974); and Japanese Patent Publication Nos. 12553/1979 and 18867/1982]. However, aspartase activity of *Escherichia coli* used in such a conventional method is not so high as it is sufficient for the industrial production of L-aspartic acid.

Under the circumstances, in order to establish an industrially advantageous method for producing L-aspartic acid, the present inventors have intensively studied. As the result, the present inventors have succeeded in the isolation of a microbial strain having very high aspartase activity in comparison with that of its parent strain by a so-called molecular cloning, i.e., by isolating a chromosomal fragment of a microorganism of the genus Escherichia which specifies aspartase activity, joining it to a plasmid and then introducing the plasmid into a microorganism of the genus Escherichia, and found that L-aspartic acid can be very efficiently produced by utilizing the microorganism thus isolated.

SUMMARY OF THE INVENTION

One object of the present invention is to provide a novel microorganism useful for the industrial production of L-aspartic acid.

Another object of the present invention is to provide an industrially advantageous method for producing L-aspartic acid.

These objects as well as other objects and advantages of the present invention will be apparent to those skilled in the art from the following description.

According to the present invention, there is provided a novel microorganism of the genus Escherichia containing a hybrid plasmid prepared by joining of a plasmid to a deoxyribonucleic acid carrying the gene for aspartase which is obtained from a microorganism of the genus Escherichia. A method for producing L-aspartic acid comprising contacting a culture of the novel microorganism, the microbial cells collected from the culture or a processed material of the microbial cells with fumaric acid and ammonia to produce L-aspartic acid and then collecting L-aspartic acid thus produced is also provided.

DISCLOSURE OF THE INVENTION

Isolation of the microorganism of the present invention

In the present invention, the microorganism to be used as the source of deoxyribonucleic acid carrying the gene for aspartase (hereinafter referred to as chromosomal DNA) is not limited to a specific one so far as it is a microorganism of the genus *Escherichia* having aspartase activity. For example, *Escherichia coli* K-12 MM294 (ATCC No. 33625), *Escherichia coli* K-12 C600r$^-$m$^-$ (ATCC No. 33525) and the like can be used.

The plasmid to be joined with the chromosomal DNA obtained from such a microorganism as the above is not limited to a specific one so far as it is capable of replicating in a microorganism of the genus Escherichia. For example, pSC101 [Proc. Natl. Acad. Sci. USA, 70, 3240 (1973)], pBR322 [Gene., 2, 95 (1977)], pBR325 [Gene., 4, 121 (1978)], pACYC177 [J. Bacteriol., 134, 1141 (1978)], pACYC184 [J. Bacteriol., 134, 1141 (1978)]and the like can be used.

As a host into which the hybrid plasmid obtained by joining the chromosomal DNA to the plasmid is to be introduced, it may be any microorganism of the genus Escherichia being capable of transformation. For example, the above microorganism as that used for the source of the chromosomal DNA can be suitably used.

In the preparation of the novel microorganism of the present invention, firstly, the chromosomal DNA is extracted from the source microorganism of the genus Escherichia having aspartase activity. The extraction of the chromosomal DNA can be readily carried out by a standard method. For example, after subjecting microbial cells of the microorganism to lysozyme treatment and treatment with a detergent [e.g., SDS, sarcosil (sodium N-lauroyl sarcosinate), etc.], the resulting lysate is deproteinized and then the chromosomal DNA is precipitated with ethanol [J. Mol. Biol., 3, 208, (1961); Biochim. Biophys. Acta, 72, 619 (1963)].

Joining of the plasmid to the chromosomal DNA thus obtained can be carried out by a standard method. For example, after the chromosomal DNA and the plasmid DNA are cut with one or more restriction endonucleases (e.g., HindIII, XhoI, BamHI, SaLI, EcoRI, EcoRV, etc.), they are treated with a ligase (e.g., T$_4$ DNA ligase, *E. coli* DNA ligase, etc.) or, depending upon the nature of the termini formed by cut, they are treated with a terminal transferase, DNA polymerase, etc. and then treated with a ligase to join the DNA strands [see Method in Enzymology, 68, 41 (1979); "Idenshi Sosa Jikken-ho", Y. Takagi ed., Kodan-sha Scientific, Japan (1980)].

The transformation with the hybrid plasmid thus obtained can be carried out, for example, by treating cells of the host microorganism with a solution containing calcium chloride at a low temperature to increase permeability of the cell membrane to introduce the hybrid DNA into the host microorganism [J. Mol. Biol., 53, 159 (1970); J. Bacteriol., 119, 1072 (1974)].

Among transformants thus obtained, the desired transformant into which the hybrid plasmid carrying the gene for aspartase has been introduced can be selected for the better growth on a medium containing L-aspartic acid as a sole carbon or nitrogen source. Further, when the transformation is carried out, it is possible to previously select the desired hybrid plasmid by introducing hybrid plasmids into microorganism mutants having various mutations. Examples of such mutants include microorganisms of the genus Escherichia having aspartase defect and they can be selected for the growth on a medium containing glutamic acid as a sole carbon source.

Thus, the desired novel microorganism of the present invention, i.e., the microorganism of the genus Escherichia containing a hybrid plasmid prepared by joining of a plasmid to a deoxyribonucleic acid carrying the gene for aspartase which is obtained from a microorganism of the genus Escherichia can be obtained.

The representatives of the microorganism of the present invention are deposited with Fermentation Research Institute (FRI), Agency of Industrial Science and Technology, Ibaragi-ken, Japan under Budapest Treaty on May, 30, 1983. They are *Escherichia coli* TA5003 (FERM BP-531) and *Escherichia coli* TA5004 (FERM BP-532). Aspartase activities of these microorganisms are about 5 to 20 times as high as that of the parent strain.

*Production of L-aspartic acid*

Since, as described in the above, aspartase activity of the microorganism of the present invention is extremely superior to that of the parent strain, L-aspartic acid can be advantageously produced from fumaric acid and ammonia by using the microorganism.

That is, L-aspartic acid can be produced by contacting a culture of the microorganism of the present invention, microbial cells collected from the culture or a processed material of the microbial cells with the substrates, i.e., fumaric acid and ammonia to effect L-aspartic acid-producing enzymatic reaction.

The microorganism of the present invention can be cultivated by using a conventional nutrient medium containing carbon sources (e.g., glucose, glycerol, fumaric acid), nitrogen sources (e.g., ammonium fumarate, ammonium sulfate), organic nutrients (e.g., yeast extract, peptone, corn steep liquor, meat extract), inorganic salts (e.g., potassium dihydrogen phosphate, magnesium sulfate), and the like. The cultivation can be carried out according to a conventional method. For example, after adjusting pH of a medium to 5.0 to 9.0, the microorganism is inoculated into the medium and incubated at 10° to 45° C., preferably, at 28 to 37° C. for 12 to 92 hours under aerobic conditions. In the medium, L-aspartic acid can be also used as a carbon source as well as a nitrogen source and the preferred amount thereof is about 0.1 to 5%.

As described in the above, when L-aspartic acid-producing reaction is carried out, not only the culture of the microorganism but also microbial cells collected from the culture and a processed material of the microbial cells can be used.

The collection of the microbial cells from the culture can be carried out according to a conventional method such as filtration, centrifugation and the like.

Examples of the processed material of the microbial cells are washed microbial cells prepared by washing the cells with physiological saline solution, phosphate buffer solution, carbonate buffer solution and the like; dried microbial cells prepared by drying the microbial cells according to a conventional method such as lyophilization, acetone treatment and the like; ground microbial cells prepared by grinding the microbial cells with glass beads, alumina and the like; autolysates of the microbial cells prepared by toluene, chloroform and the like; sonicates of the microbial cells prepared by a sonic oscillator; microbial cell extracts prepared by french press; and immobilized preparations obtained by immobilizing the microbial cells or the above other processed materials thereof according to a known method such as gel conjugation method, adsorption method or the like. Examples of the immobilized preparations are those obtained by immobilizing the microbial cells or the above other processed materials thereof on supports, carriers or bases such as polyacrylamide gel, sulfur-containing polysaccharide (e.g., carrageenan, furcellaran, etc.) gel, collagen gel, alginic acid gel, polyvinyl alcohol gel, agar gel and the like. When polyacrylamide gel is used, the immobilization can be carried out according to the method disclosed in Japanese Patent Publication No. 1831/1978. When sulfur-containing polysaccharide gel is used, the method disclosed in Japanese Patent Laid Open Publication No. 6483/1978 can be employed. Further, when collagen gel, alginic acid gel, polyvinyl alcohol gel, agar gel or the like is used, the immobilization can be carried out according to the methods disclosed in Japanese Patent Laid Open Publication Nos. 144780/1976, 30582/1974, 80285/1974 and 133484/1976.

Fumaric acid and ammonia to be used as the substrates can be introduced into a L-aspartic acid-producing enzymatic reaction system in various forms. For example, they can be introduced into the reaction system in the form of ammonium fumarate, or as fumaric acid or its salt and an inorganic ammonium salt.

As the salt of fumaric acid, for example, sodium fumarate or potassium fumarate can be suitably used. As the inorganic ammonium salt, for example, ammonium chloride, ammonium sulfate, ammonium phosphate or a mixture thereof can be suitably used.

In case of using fumaric acid or its salt and the inorganic ammonium salt, it is preferable that the molar ratio of these two components are within the range between 1:1.5 to 1:2.

The enzymatic reaction can be carried out at such a wide temperature range as about 5 to 50° C. but, in view of stability of the enzyme of the microorganism, it is preferable that the enzymatic reaction is carried out at 20 to 45° C. Further, it is preferable to carry out the enzymatic reaction at a pH range of 6 to 10. Besides, when the enzymatic reaction is carried out, it is preferable to add a divalent metal ion such as calcium ion, magnesium ion, manganese ion, strontium ion or the like to the reaction system. The amount of the divalent metal ion can be about 0.1 to 10 mM and thereby stability of the enzyme can be improved.

When the microbial cells are used, preferably, the reaction is carried out in batchwise and L-aspartic acid is produced by suspending the microbial cells collected from the culture thereof in a solution of the above substrates and stirring the suspension. When the immobilized preparation is used, the reaction can be carried out not only by a batch process but also by a continuous process using a column packed with the immobilized preparation since the immobilized preparation is insoluble in water. For example, the immobilized preparation is packed in a column and a substrate solution is passed down through the column at a suitable flow rate to obtain an effluent containing only L-aspartic acid. When the reaction is carried out by a batch process, L-aspartic acid is produced by suspending the immobilized preparation in a substrate solution and stirring the suspension. In the latter case, the immobilized preparation can be reused by separating it from the reaction mixture according to a standard method such as filtration or centrifugation. The progress of the above reaction is effected by the amount of microbial cells, temperature, reaction time, flow rate of the substrate (particularly, linear velocity) and the like. Optimum reaction conditions which can attain 100% progress of the reaction can be readily found, for example, by suitably adjusting the flow rate of a substrate solution passing down through a column according to the amount of an immobilized preparation, in case of a continuous process using a column; or by suitably adjusting a reaction time, in case of a batch process.

L-Aspartic acid thus produced and accumulated in the reaction mixture can be readily separated and purified according to known methods, for example, by combining a conventional method using an ion exchange resin with other known methods.

As described hereinbefore, according to the present invention, the microorganism of the genus Escherichia having extremely high aspartase activity in comparison with that of a known microorganism of the genus Escherichia used in a conventional method for producing L-aspartic acid can be obtained and, by using the microorganism of the present invention, L-aspartic acid can be advantageously produced in an industrial scale.

The following examples further illustrate the present invention in detail but are not to be construed to limit the scope thereof.

In the examples, aspartase activity was determined by contacting 1 M ammonium fumarate solution containing 1 mM magnesium chloride (pH 8.5) with the microbial cells or the processed material thereof, incubating at 37° C. for 1 hour to effect the enzymatic reaction, and measuring L-aspartic acid in the resulting reaction mixture by a bioassay using *Leuconostoc mesenteroides* P60 [J. Biol. Chem., 172, 15 (1948)].

EXAMPLE 1

(1) Preparation of chromosomal DNA

*Escherichia coli* K-12 MM294 was inoculated into L-broth (1.2 liters, peptone 1%, yeast extract 0.5%, sodium chloride 0.5%, pH 7.0) containing glucose (0.2 %) and incubated with shaking at 37° C. for 8 hours. After incubation, microbial cells in the logarithmic growth phase were collected by centrifugation. The microbial cells were lysed by lysozyme treatment and sarcosil treatment, deproteinized by phenol treatment and then treated with ethanol to precipitate chromosomal DNA. According to a conventional method, the precipitated chromosomal DNA was extracted and purified to obtain the desired chromosomal DNA (5.4 mg).

(2) Preparation of plasmid DNA

*Escherichia coli* K-12 C600r$^-$m$^-$ containing pSC101 [Proc. Natl. Acad. Sci. USA, 70, 3240 (1973)] was inoculated into L-broth (800 ml) containing glucose (0.2 %) and incubated with shaking at 37° C. for 7 hours. The microbial cells were collected by centrifugation. The cells were lysed by lysozyme treatment and SDS treatment and, after addition of sodium chloride in such an amount that the final concentration being 1 M, the mixture was centrifuged at 100,000×g for 30 minutes. After collection of the supernatant and treatment with phenol-chloroform, ethanol was added thereto and DNA was collected by centrifugation. The precipitated DNA was dissolved in 10 mM Tris HCl/1 mM EDTA (pH 7.5) and the solution was subjected to cesium chloride - ethidium bromide equilibrium density gradient centrifugation to separate and purify the plasmid DNA. Thus, pSC101 plasmid DNA (1.0 mg) was obtained.

(3) Preparation of hybrid plasmid

Each of the chromosomal DNA (10 μg) obtained in the above (1) and the plasmid DNA (2 μg) obtained in the above (2) was treated with both restriction endonucleases EcoRI and XhoI, simultaneously, under normal conditions to completely cut the DNA strands. After heat treatment at 65° C. for 10 minutes, both reaction mixtures were combined and the T$_4$ DNA ligase was effected under normal conditions to join the DNA strands.

(4) Transformation with hybrid plasmid (a) *Escherichia coli* K-12 C600r$^-$m$^-$ was subjected to mutagenesis with N-methyl-N'-nitro-N-nitrosoguanidine and spread on minimum agar medium plates (dipotassium hydrogen phosphate 0.7%, potassium dihydrogen phosphate 0.3%, ammonium sulfate 0.1%, magnesium sulfate heptahydrate 0.01% agar 1.5%) containing L-glutamic acid (30 mM) as a carbon source. After incubation at 37° C. for 2 days, among the resulting colonies, a large colony was picked up and isolated to obtain TK6 strain. TK6 strain was then subjected to mutagenesis with N-methyl-N'-nitro-N-nitrosoguanidine and spread on L-broth agar plates containing glucose (0.2%) in such an amount that about 100 colonies per plate appearing. Among the resulting colonies, the strain which did not grow on the minimum agar medium plates containing L-glutamic acid (30 mM) as a carbon source by incubation at 37° C. for 2 days was selected (replica technique) to obtain TK237 strain having aspartase defect.

Strain TK237 thus obtained was inoculated into L-broth (30 ml) containing glucose (0.2 %) and incubated with shaking at 37° C. until the growth was reached the middle of the logarithmic growth phase. The microbial cells were collected and suspended in an ice-cold 0.1 M magnesium chloride solution (15 ml). After collection of the cells, they were resuspended in an ice-cold 0.1 M potassium chloride solution (15 ml). After allowing to stand at 0° C. for 20 minutes, the cells were collected and suspended in an ice-cold 0.1 M calcium chloride solution (3 ml). To the cell suspension was added the DNA solution obtained in the above (3). The mixture was ice-cooled for 60 minutes and subjected to heat treatment at 37° C. for 3 minutes to introduce DNA into the cells. Then, to this suspension was added L-broth (15 ml) containing glucose (0.2 %) and the mixture was incubated with shaking at 37° C. for 2 hours. The cells were collected and suspended in physiological saline solution (15 ml). Again the cells were collected and suspended in physiological saline solution (15 ml). After collection of the cells, they were resuspended in physiological saline solution (15 ml) and 0.5 to 1 ml aliquots thereof were spread on agar plates containing L-glutamic acid (30 mM) as a carbon source and tetracycline (5 μg/ml) and incubated at 37° C. for 7 days.

Among the resulting colonies, one having higher aspartase activity than that of strain TK6 was isolated as the transformant with the hybrid plasmid DNA. After incubation of the transformant thus obtained in L-broth (1 liter), the hybrid plasmid DNA was collected according to the same manner as in the above (2).

(b) The hybrid plasmid DNA thus obtained and strain TK6 were treated according to the same manner as in the above (a) to isolate the transformant. The cells thus treated were spread on L-broth agar medium plates containing tetracycline (5 μg/ml) and incubated at 37° C. overnight to obtain the desired transformant, *Escherichia coli* TA5003 (FERM BP-531). This strain contained the hybrid plasmid DNA (pTA503) having the gene for aspartase and had high aspartase activity.

Aspartase activities of *Escherichia coli* TA 5003 thus obtained and the parent strain, *Escherichia coli* K-12

MM294, were measured. The results are shown in Table 1.

TABLE 1

| Microorganisms | Aspartase activity (μmoles/min/mg protein) |
| --- | --- |
| E. coli TA5003 | 91 |
| E. coli K-12 MM294 | 13 |

Medium: ammonium fumarate 3%, potassium dihydrogen phosphate 0.2%, magnesium sulfate heptahydrate 0.05%, corn steep liquor 2%, yeast extract 2% (pH 7.0).

As is seen from Table 1, in comparison with the parent strain, Escherichia coli K-12 MM294, the aspartase activity of the microorganism of the present invention, Escherichia coli TA5003 is increased about 7 times.

EXAMPLE 2

(1) Preparation of plasmid DNA

According to the same manner as in Example 1(2), the plasmid pBR322 DNA (1.0 mg) was obtained by substituting the plasmid pBR322 for pSC101. On the other hand, Escherichia coli TA5003 prepared in Example 1 was treated according to the same manner as in Example 1(2) to obtain the plasmid pTA503 DNA (0.6 mg).

(2) Preparation of hybrid plasmid (a) Each of plasmid pBR322 DNA obtained in (1) (15 μg) and pTA503 DNA (15 μg) was treated with two restriction endonucleases, BamHI and SalI, simultaneously, under normal conditions to cut both DNA strands. After heat treatment at 65° C. for 10 minutes, both reaction mixtures were combined and treated with T4 DNA ligase under normal conditions to join the DNA strands.

(b) Escherichia coli TK237 was transformed with the DNA solution obtained in (2)(a). The resulting strain was grown in L-broth containing glucose (0.2%) and ampicillin (50 μg/ml) at 37° C. for 8 hours and treated according to the same manner as in Example 1(2) to obtain a hybrid plasmid DNA (0.7 mg). The hybrid plasmid DNA thus obtained was treated with the restriction endonuclease, EcoRV, under normal conditions to cut the plasmid DNA strand. After heat treatment at 65° C. for 10 minutes, the reaction mixture was treated with T4 DNA ligase under normal conditions to join the DNA strands.

(3) Transformation with hybrid plasmid

According to the same manner as in Example 1(4), strain TK237 was transformed with the DNA solution of the above (2) and a microbial strain which was capable of growing on L-broth agar plates containing glucose (0.2%) and ampicillin (50 μg/ml) was isolated to select a microorganism having high aspartase activity. Thus, there was obtained the desired transformant, Escherichia coli TA 5004 (FERM BP-532). This strain contains the hybrid plasmid (pTA504) having the gene for aspartase and has high aspartase activity.

Aspartase activities of Escherichia coli TA 5004 and the parent strain, Escherichia coli K-12MM294 were measured. The results are shown in Table 2.

TABLE 2

| Microorganisms | Aspartase activity (μmoles/min/mg protein) |
| --- | --- |
| E. coli TA5004 | 190 |
| E. coli K-12 MM294 | 13 |

The medium was the same as that used in Table 1.

As is seen from Table 2, in comparison with the parent strain, Escherichia coli K-12 MM294, the aspartase activity of Escherichia coli TA5004 is increased about 15 times.

Further, the hybrid plasmid pTA504 of Escherichia coli TA5004 was extracted and the DNA strand was simultaneously cut with both restriction endonucleases EcoRV and SalI. The resulting DNA fragments were analyzed by standard agarose gel electrophoresis. As the result, it has been found that pTA504 is composed of the larger DNA fragment formed by cleavage of pBR322 plasmid DNA with EcoRV and SalI and the DNA fragment derived from pTA503.

EXAMPLE 3

Escherichia coli TA 5004 was inoculated into a medium (500 ml, pH 7.0) containing ammonium fumarate (3%), potassium dihydrogen phosphate (0.2%), magnesium sulfate heptahydrate (0.05%), corn steep liquor (4%) and yeast extract (2%) and incubated with shaking at 37° C. for 24 hours. The resulting culture was adjusted to pH 8.5 with aqueous ammonia. Ammonium fumarate (65 g) and Triton X-100 (500 mg) were added to the culture and incubation was further continued at 37° C. for 6 hours to conduct the enzymatic reaction. The reaction mixture was filtered, concentrated and adjusted to pH 2.8 to precipitate crude crystals of L-aspartic acid. The crude crystals were filtered off and recrystallized from water to give L-aspartic acid (47.0 g).

EXAMPLE 4

(1) Escherichia coli TA 5004 was inoculated into a medium (pH 7.0) containing ammonium fumarate (3%), potassium dihydrogen phosphate (0.2%), magnesium sulfate heptahydrate (0.05%), corn steep liquor (4%) and yeast extract (2%) and incubated with shaking at 37° C. for 24 hours. The resulting culture was centrifuged to collect microbial cells and the cells were suspended in physiological saline solution (16 ml). To the suspension was added 3.2% aqueous solution of GENU GEL WG (carrageenan manufactured by Kopenhagen Pectin Factory Ltd.) (64 ml) previously warmed at 40° C. and thoroughly mixed in a warm water bath. The resulting mixture was added dropwise to 1 M aqueous ammonium fumarate solution containing 1 mM magnesium chloride (pH 8.5) to give immobilized Escherichia coli (61 g, wet weight) having aspartase activity in globular gel (about 3 mm diameter). The aspartase activity per 1 g of the resulting immobilized cells was 22.3 m moles/hr.

(2) The immobilized Escherichia coli prepared in the above (1) (61 g) was packed in a jacketed column (4 cm×8 cm) and incubated at 37° C. for 48 hours to activate the immobilized cells (aspartase activity: 1980 m moles/hr). After activation, 1 M ammonium fumarate solution containing 1 mM magnesium chloride (pH 8.5, 1,000 ml) was passed through the column at 37° C. at the flow rate of 50 ml/hr. The effluent was adjusted to pH 2.8 to precipitate crystals and the crystals were filtered off to give L-aspartic acid (128 g).

EXAMPLE 5

(1) The microbial cells of *Escherichia coli* TA 5004 (8 g) were suspended in physiological saline solution (5 ml). To the suspension was added 2.2% aqueous solution of GENU GEL WG containing 1% locust bean gum (80 ml) previously warmed at 40° C. and mixed. The resulting mixture was gelled by cooling. Further, 2% aqueous potassium chloride solution (25 ml) was slowly added and the mixture was allowed to stand for 30 minutes. The gel was shaped into cubes of 3 mm in side length and washed with 2% aqueous potassium chloride solution. The gel (91 g) thus obtained was dipped in cold ethanol (100 ml) and added thereto glutaraldehyde in such an amount that the final concentration thereof was 0.49%. The mixture was allowed to stand with ice-cooling for 15 minutes. Then, the gel was filtered off and washed with 2% aqueous potassium chloride solution. After washing, the gel was activated to obtain an immobilized *Escherichia coli* having aspartase activity (87 g, wet weight). The aspartase activity per 1 g of the resulting immobilized cells was 30.0 m moles/hr.

(2) The immobilized *Escherichia coli* obtained in the above (1) (11 g) was packed in a jacketed column (1.6 cm ×12 cm) and 1 M aqueous ammonium fumarate solution containing 1 mM magnesium chloride (pH 8.5) was continuously passed through the column at 37° C. at the flow rate of 6 ml/hr. Stability of aspartase activity in the immobilized cells was evaluated by measuring the aspartase activity of samples of the effluent at intervals time. As the result, even after 20 days, decrease of the activity was not observed.

EXAMPLE 6

The microbial cells of *Escherichia coli* TA5004 (10 g) was suspended in 0.05 M phosphate buffer (pH 8.5, 50 ml) and sonicated at 9 Kc for 15 minutes. Then, the suspension was centrifuged and the resulting supernatant (40 ml) was passed through a column packed with Duolite-A7 (a weak basic anion exchange resin manufactured by Diamond Shamrock Chemical Co. in U.S.A.) (60 ml) at room temperature at 30 ml/hr. Then, the column was subjected to cross-linking treatment with a solution containing 0.1 M phosphate buffer (pH 8.5, 300 ml) and 0.4% glutaraldehyde (300 ml) for 30 minutes and excess glutaraldehyde was thoroughly washed out to give an immobilized enzyme. The immobilized enzyme was packed in a column (volume 50 ml) and 1 M ammonium fumarate solution containing 1 mM magnesium chloride (pH 8.5, 500 ml) was passed through the column at the flow rate of 25 ml/hr. The combined effluent was adjusted to pH 2.8 to precipitate crystals. The crystals were filtered off to give L-aspartic acid (55 g).

EXAMPLE 7

According to the same manner as in Example 6, a supernatant was obtained by using *Escherichia coli* TA 5004. The supernatant was subjected to ammonium sulfate fractionation (saturation degree: 30 to 50%) and the resulting precipitate was dissolved in water (5 ml). The solution was dialyzed overnight against water and the resulting dialysate was taken as an enzyme solution (standard aspartase). The enzyme solution (2 ml) and 3.2% aqueous GENU GEL WG solution (12 ml) were mixed in a warm water bath at 37° C. The mixture was added dropwise to 2% aqueous potassium chloride solution to give globular gel (about 3 mm diameter). The aspartase activity of the resulting immobilized aspartase was 18.7 m moles/hr/g.

What is claimed is:

1. *Escherichia coli* TA-5004 (FERM BP-532).

2. A method for producing L-aspartic acid which comprises the steps of:
   (I) culturing *Escherichia coli* TA-5004 (FERM BP-532);
   (II) contacting fumaric acid and ammonia with
      (a) a culture obtained in the step (I).
      (b) microbial cells collected from the culture, or
      (c) a processed material of the microbial cells,
   (III) incubating said culture, cells or processed material under conditions sufficient to produce L-aspartic acid; and then
   (IV) collecting L-aspartic acid thus produced.

3. A method of claim 2, wherein fumaric acid and ammonia are used in the form of ammonium fumarate.

* * * * *